United States Patent
Koehler

(10) Patent No.: US 11,107,599 B2
(45) Date of Patent: Aug. 31, 2021

(54) DIFFRACTION GRATING FOR X-RAY PHASE CONTRAST AND/OR DARK-FIELD IMAGING

(71) Applicant: KONINKLIJKE PHILIPS N.V., Eindhoven (NL)

(72) Inventor: Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/644,178

(22) PCT Filed: Aug. 24, 2018

(86) PCT No.: PCT/EP2018/072833
§ 371 (c)(1),
(2) Date: Mar. 4, 2020

(87) PCT Pub. No.: WO2019/048252
PCT Pub. Date: Mar. 14, 2019

(65) Prior Publication Data
US 2021/0065923 A1 Mar. 4, 2021

(30) Foreign Application Priority Data
Sep. 6, 2017 (EP) .................................. 17189540

(51) Int. Cl.
*G01N 23/04* (2018.01)
*A61B 6/00* (2006.01)
(Continued)

(52) U.S. Cl.
CPC ............ *G21K 1/062* (2013.01); *A61B 6/4042* (2013.01); *A61B 6/4291* (2013.01); *A61B 6/484* (2013.01);
(Continued)

(58) Field of Classification Search
None
See application file for complete search history.

(56) References Cited

U.S. PATENT DOCUMENTS 7,983,381 B2  7/2011  David
8,908,274 B2  12/2014  Teshima
(Continued)

FOREIGN PATENT DOCUMENTS

WO    WO2017036729 A1    3/2017

OTHER PUBLICATIONS

PCT International Search Report, International application No. PCT/EP2018/072833, dated Nov. 26, 2018.
(Continued)

*Primary Examiner* — Thomas R Artman
(74) *Attorney, Agent, or Firm* — Larry Liberchuk

(57) ABSTRACT

The present invention relates to a grating for X-ray phase contrast and/or dark-field imaging. It is described to form a photo-resist layer on a surface of a substrate. The photo-resist layer is illuminated with radiation using a mask representing a desired grating structure. The photo-resist layer is etched to remove parts of the photo-resist layer, to leave a plurality of trenches that are laterally spaced from one across the surface of the substrate. A plurality of material layers are formed on the surface of the substrate. Each layer is formed in a trench. A material layer comprises a plurality of materials, wherein the plurality of materials are formed one on top of the other in a direction perpendicular to the surface of the substrate. The plurality of materials comprises at least one material that has a k-edge absorption energy that is higher than the k-edge absorption energy of Gold and the plurality of materials comprises Gold.

15 Claims, 3 Drawing Sheets

(51) Int. Cl.
*G21K 1/06* (2006.01)
*G01N 23/041* (2018.01)
*G01N 23/20008* (2018.01)
*G03F 7/09* (2006.01)

(52) U.S. Cl.
CPC ..... *G01N 23/041* (2018.02); *G01N 23/20008* (2013.01); *G03F 7/094* (2013.01); *G21K 2207/005* (2013.01)

(56) References Cited

U.S. PATENT DOCUMENTS

| | | | | |
|---|---|---|---|---|
| 8,999,435 | B2* | 4/2015 | Setomoto | B29D 11/00769 |
| | | | | 427/160 |
| 9,206,309 | B2* | 12/2015 | Appleby | B22C 9/04 |
| 9,230,703 | B2 | 1/2016 | Mohr | |
| 9,315,663 | B2* | 4/2016 | Appleby | B22C 9/04 |
| 10,207,315 | B2* | 2/2019 | Appleby | B29C 33/38 |
| 2010/0246769 | A1 | 9/2010 | David | |
| 2011/0052800 | A1* | 3/2011 | Setomoto | B29D 11/00769 |
| | | | | 427/162 |
| 2011/0189440 | A1* | 8/2011 | Appleby | B29C 33/301 |
| | | | | 428/156 |
| 2012/0051508 | A1* | 3/2012 | Kaneko | G21K 1/025 |
| | | | | 378/62 |
| 2012/0051509 | A1* | 3/2012 | Kaneko | A61B 6/4291 |
| | | | | 378/62 |
| 2013/0142307 | A1 | 6/2013 | Nakamura | |
| 2013/0148788 | A1* | 6/2013 | Mohr | G21K 1/06 |
| | | | | 378/156 |
| 2013/0338267 | A1* | 12/2013 | Appleby | B29C 33/301 |
| | | | | 523/458 |
| 2015/0117599 | A1 | 4/2015 | Yun | |
| 2016/0082502 | A1* | 3/2016 | Appleby | C08L 63/00 |
| | | | | 164/369 |
| 2021/0065923 | A1* | 3/2021 | Koehler | G21K 1/062 |

OTHER PUBLICATIONS

Ya0hu Lei et al: "Fabrication of X-Ray Absorption Gratings Via Micro-Casting for Grating-Based Phase Contrast Imaging", Journal of Micromechanics & Microengineering, Institute of Physics Publishing, Bristol, GB, vol. 24, No. 1, Nov. 27, 2013 (Nov. 27, 2013), p. 15007, XP02O255919.

Yang Du et al; "A Low Cost Method for Hard X-Ray Grating Interferometry", Physics in Medicine and Biology, Institute of Physics Publishing, Bristol GB, vol. 61, No. 23, Nov. 3, 2016 (Nov. 3, 2016), pp. 8266-8275, XP020311310.

Romano L et al: "High Aspect Ratio Metal Microcasting by Hot Embossing for X-Ray Optics Fabrication", Microelectronic Engineering, vol. 176, Jan. 3, 2017 (Jan. 3, 2017), pp. 6-10, XP085017405.

* cited by examiner

DIFFRACTION GRATING FOR X-RAY PHASE CONTRAST AND/OR DARK-FIELD IMAGING

FIELD OF THE INVENTION

The present invention relates to a diffraction grating for phase contrast and/or dark-field imaging, to an X-ray phase contrast and/or dark-field system, and to a method of manufacturing a diffraction grating for X-ray phase contrast and/or dark-field imaging.

BACKGROUND OF THE INVENTION

Differential phase contrast and dark-field imaging (DPCI and DFI) are promising technologies that will likely enhance the diagnostic quality of X-ray equipment Computer Tomography (CT) and radiography systems. A conventional X-ray source can be used with a Talbot-Lau interferometer and a conventional X-ray detector. However, key components are the gratings, particularly the source grating (G0) and analyzer grating (G2). The current standard for manufacturing gratings is the "Lithography, Electroplating and Molding" LIGA technology, with gratings made from Gold. The gratings, which have deep trenches between the Gold layers forming the grating, are expensive and difficult to align. Such gratings are made from Gold, because Gold exhibits excellent absorption over a large range of relevant energies due to its high density of 19.3 g/cm$^3$, which enables the layer thicknesses to be kept as less high as possible.

US2015/117599A1 describes an x-ray interferometric imaging system in which the x-ray source comprises a target having a plurality of structured coherent sub-sources of x-rays embedded in a thermally conducting substrate. The system additionally comprises a beam-splitting grating G1 that establishes a Talbot interference pattern, which may be a π phase-shifting grating, and an x-ray detector to convert two-dimensional x-ray intensities into electronic signals. The system may also comprise a second analyzer grating G2 that may be placed in front of the detector to form additional interference fringes, and a means to translate the second grating G2 relative to the detector. In some embodiments, the structures are microstructures with lateral dimensions measured on the order of microns, and with a thickness on the order of one half of the electron penetration depth within the substrate. In some embodiments, the structures are formed within a regular array.

WO2017/036729A proposes a method with several options to manufacture high aspect ratio structures. The method is based on fabrication of high aspect ratio recess structure in silicon by dry or chemical etching and then filling the high aspect ratio recess with metal by using electroplating, atomic layer deposition, wafer bonding, metal casting or combination of these techniques. The gratings can be used for x-ray or neutron imaging, as well as for space applications.

US2013/142307A1 describes an X-ray imaging apparatus that includes a diffraction grating that forms an interference pattern by diffracting X-rays emitted from an X-ray source, an absorption grating that shields a portion of the interference pattern, a detector that detects the X-rays emitted from the absorption grating, and a moving unit that changes relative positions of a sample object and the absorption grating. The moving unit changes the relative positions of the sample object and the absorption grating from first relative positions to second relative positions. The detector detects the X-rays at least when the sample object and the absorption grating are at the first relative positions and when the sample object and the absorption grating are at the second relative positions.

However, there is a need to improve such gratings and how they are manufactured, and do so in a manner that is less expensive than the current Gold standard.

SUMMARY OF THE INVENTION

It would be advantageous to have improved diffraction grating for phase contrast and/or dark-field imaging and method of manufacturing a diffraction grating for phase contrast and/or dark-field imaging.

The object of the present invention is solved with the subject matter of the independent claims, wherein further embodiments are incorporated in the dependent claims. It should be noted that the following described aspects and examples of the invention apply also to the diffraction grating for phase contrast and/or dark-field imaging, the phase contrast and/or dark-field imaging system, the method for manufacturing a diffraction grating for phase contrast and/or dark-field imaging.

According to a first aspect, there is provided a grating for X-ray phase contrast and/or dark-field imaging, the grating comprising:

a substrate; and a plurality of material layers.

The plurality of material layers are formed on a surface of the substrate. The plurality of material layers are also laterally spaced from one another across the surface of the substrate. A material layer of the plurality of material layers comprises a plurality of materials. The plurality of materials are formed one on top of the other in a direction perpendicular to the surface of the substrate. The plurality of materials comprises at least one material that has a k-edge absorption energy that is higher than the k-edge absorption energy of Gold. The plurality of materials also comprises Gold.

In this way, because Gold is extremely expensive the grating is made from a material other than Gold, which has a k-edge absorption edge above that of Gold, but augmented with a Gold layer. In this way, the analyzer grating G2 and/or source grating G0 used in phase contrast and/or dark field imaging can have in particular an improved reduction in transmission at lower energies than that achievable through the use of the other material only grating. In particular the transmission below the k-edge of the other material and above the k-edge of gold at 80.7 keV is improved.

Additionally, the absolute layer thicknesses can be reduced over that for the other material alone (less deep gratings are required), which relaxes the alignment process required when setting up a phase contrast and/or dark-field imaging system, providing for improved imaging and a reduction in the time required to set up the imaging system.

In an example, a material of the at least one material that has a k-edge absorption energy that is higher than the k-edge absorption energy of Gold is Lead.

Thus, the k-edge of Lead at 88.0 keV is used to complement that of Gold at 80.7 keV to improve the required low transmission of the G2 and/or G0 grating at high energies.

In an example, a material of the at least one material that has a k-edge absorption energy that is higher than the k-edge absorption energy of Gold is Bismuth.

Thus, the k-edge of Bismuth at 90.5 keV is used to complement that of Gold at 80.7 keV to improve the required low transmission of the G2 and/or G0 grating at high energies, and this can further be used in combination with the k-edge of Lead at 88.0 keV to provide further improvement in the required low transmission of the G2 and/or G0 grating at high energies.

In an example, the plurality of materials comprises at least one material that has a k-edge absorption energy that is lower than the k-edge absorption energy of Gold.

In this way, the analyzer grating G2 and/or source grating used in phase contrast and/or dark field imaging can have an improved reduction in transmission at both higher energies and lower energies than that achievable through the use of a grating that is made of a material other than Gold (but that has a higher k-edge). Also, the grating can have an improved reduction in transmission over a Gold only grating. By using one or indeed more than one material that has a k-edge absorption energy above that of Gold at 80.7 keV and by using one or indeed more than one material that has a k-edge absorption energy below that of Gold means that design flexibility is provided in order to obtain the required low transmissions over a broad energy range both above 80.7 keV and below this energy. In this manner, the presence of k-edges in different materials that are above and below that of Gold are leveraged in order to provide an improved grating design.

In an example, a material of the at least one material that has a k-edge absorption energy that is lower than the k-edge absorption energy of Gold is Tungsten.

In an example, a material of the at least one material that has a k-edge absorption energy that is lower than the k-edge absorption energy of Gold is Iron.

In an example, a material of the at least one material that has a k-edge absorption energy that is lower than the k-edge absorption energy of Gold is a Tungsten-Iron alloy.

In an example, the plurality of material layers are laterally spaced from one another by a plurality of resist layers.

In other words, because the grating itself in terms of the material layers has improved performance, the requirement to remove the resist layer that exists between those layers can be dispensed with if necessary. This provides for simplification of the manufacturing process, and to a grating that is more robust because the material layers are not free standing, but butt up against resist layers.

In an example, a thickness of Gold in the material layer of the plurality of material layers is less than 10% of a total thickness of the material layer.

Thus, the amount of Gold required is significantly reduced over that required for Gold only G2 gratings, leading to a significant reduction in cost.

According to a second aspect, there is provided an X-ray phase contrast and/or dark-field system comprising a diffraction grating for X-ray phase contrast and/or dark-field imaging according to any of the preceding claims.

According to a third aspect, there is provided a method of manufacturing a grating for X-ray phase contrast and/or dark-field imaging, the method comprising:
a) forming a photo-resist layer on a surface of a substrate;
b) illuminating the photo-resist layer with radiation using a mask representing a desired grating structure;
c) etching the photo-resist layer to remove parts of the photo-resist layer, to leave a plurality of trenches that are laterally spaced from one across the surface of the substrate;
d) forming a plurality of material layers on the surface of the substrate, wherein each layer is formed in a trench, wherein a material layer comprises a plurality of materials, wherein the plurality of materials are formed one on top of the other in a direction perpendicular to the surface of the substrate, and wherein the plurality of materials comprises at least one material that has a k-edge absorption energy that is higher than the k-edge absorption energy of Gold and comprises Gold.

In an example, at least one material that has a k-edge absorption energy that is higher than the k-edge absorption energy of Gold is Lead and/or Bismuth.

In an example, in step d) the plurality of materials comprises at least one material that has a k-edge absorption energy that is lower than the k-edge absorption energy of Gold.

In an example, the at least one material that has a k-edge absorption energy that is lower than the k-edge absorption energy of Gold is Tungsten and/or Iron and/or a Tungsten-Iron alloy.

In an example, the method comprises step e) removing a plurality of resist layers that are between the plurality of material layers.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
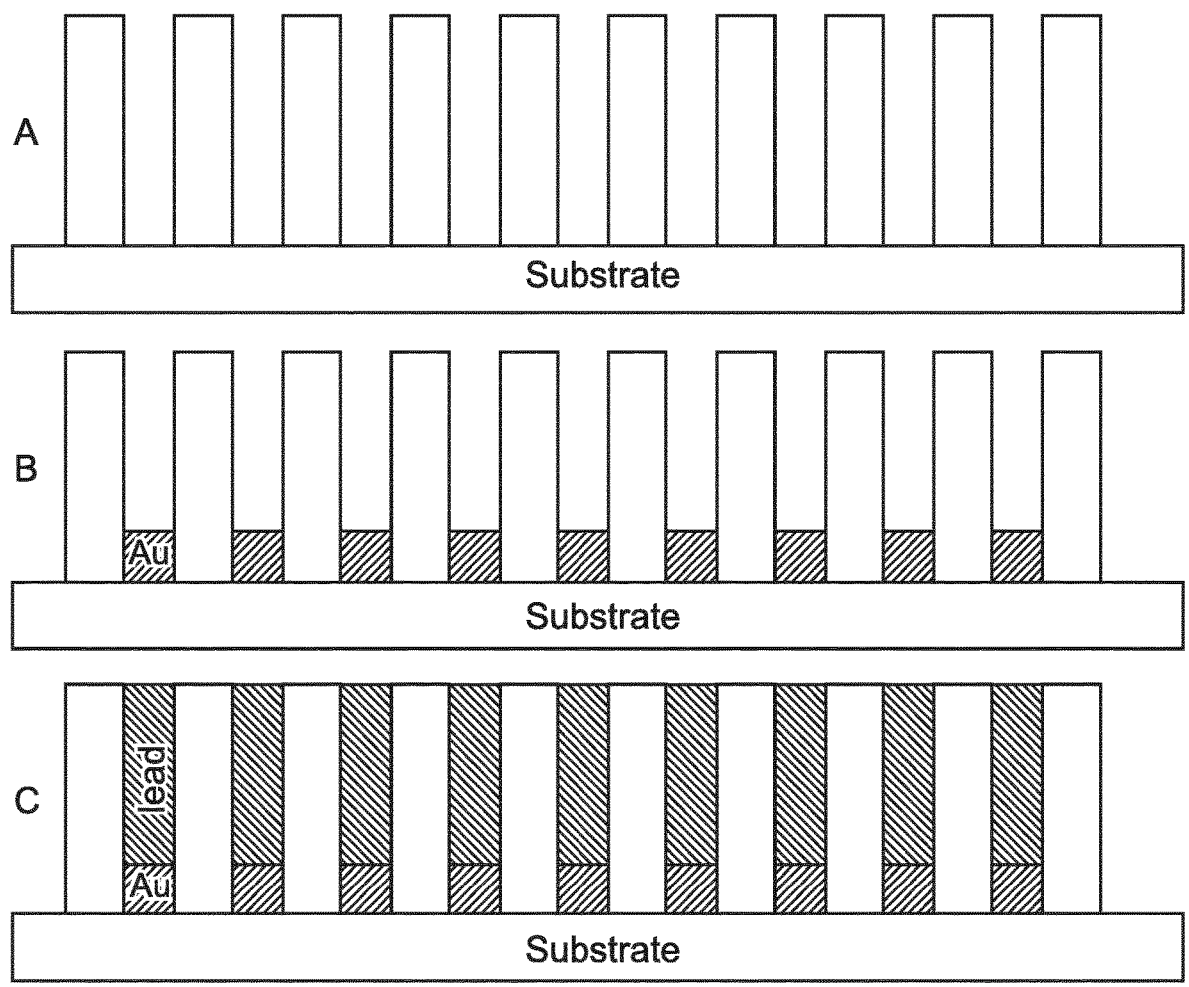
FIG. 1 shows a schematic set up of an example of a parts of a manufacturing process for a diffraction grating for phase contrast and/or dark-field imaging.

FIG. 1 shows an example of parts of a method of manufacturing a grating for phase contrast and/or dark-field imaging. FIG. 1 shows the end results at different stages of the method and does not show all the method step. However, the following description relates to a complete method, where at appropriate points in that method reference is made to the specific diagrams shown in FIG. 1. The method comprises a first step termed step a), which is the forming of a photo-resist layer on a surface of a substrate. The photo-resist is deposited onto a metallic substrate or onto a substrate with a metallic surface, which enables the latter layers to be formed by electroplating. Following step a) in step b), the method involves illuminating the photo-resist layer with radiation using a mask representing a desired grating structure. X-rays are used for illumination. Then in step c) the photo-resist layer is etched to remove parts of the photo-resist layer that have not been illuminated, to leave a plurality of trenches that are laterally spaced from one across the surface of the substrate. This is result is represented in the top drawing "A" of FIG. 1. The method of manufacture continues with step d), the forming of a plurality of material layers on the surface of the substrate. Each layer is formed in a trench, through electroplating. A material layer comprises a plurality of materials, and the plurality of materials are formed one on top of the other in a direction perpendicular to the surface of the substrate. The plurality of materials comprises Gold. The result of this step is shown in the middle drawing "B" of FIG. 1. The at least one material also comprises a material that has a k-edge absorption energy that is higher than the k-edge absorption energy of Gold. The result of this step is shown in the bottom drawing "C" of FIG. 1.

According to an example, the at least one material that has a k-edge absorption energy that is higher than the k-edge absorption energy of Gold is Lead and/or Bismuth.

According to an example, in step d) the plurality of materials comprises at least one material that has a k-edge absorption energy that is lower than the k-edge absorption energy of Gold.

According to an example, the at least one material that has a k-edge absorption energy that is lower than the k-edge absorption energy of Gold is Tungsten and/or Iron and/or a Tungsten-Iron alloy.

According to an example, the method comprises step e) which is removing a plurality of resist layers that are between the plurality of material layers. Thus referring to drawing "C" of FIG. 1, the resist layers between the lead/Au layers are removed.

Thus a grating for X-ray phase contrast and/or dark-field imaging is provided, which comprises a substrate, a plurality of material layers. The plurality of material layers are formed on a surface of the substrate. The plurality of material layers are laterally spaced from one another across the surface of the substrate. A material layer of the plurality of material layers comprises a plurality of materials. The plurality of materials are formed one on top of the other in a direction perpendicular to the surface of the substrate. And the plurality of materials comprises at least one material that has a k-edge absorption energy that is higher than the k-edge absorption energy of Gold and comprises Gold.

In an example, a thickness of the at least one material that has a k-edge absorption energy that is higher than the k-edge absorption energy of Gold in the material layer of the plurality of material layers is greater than 70% of a total thickness of the material layer. In other words, the thickness of Gold is less than 30% of the total thickness and thus in addition to providing improved reduction in transmission at high energies there is a significant reduction in the cost of the grating, such as the source grating G0 or analyzer grating G2.

In an example, the grating is a source grating G0. In an example, the grating is an analyzer (G2) grating.

According to an example, a material of the at least one material that has a k-edge absorption energy that is higher than the k-edge absorption energy of Gold is Lead.

According to an example, a material of the at least one material that has a k-edge absorption energy that is higher than the k-edge absorption energy of Gold is Bismuth.

According to an example, the plurality of materials comprises at least one material that has a k-edge absorption energy that is lower than the k-edge absorption energy of Gold.

According to an example, a material of the at least one material that has a k-edge absorption energy that is lower than the k-edge absorption energy of Gold is Tungsten.

According to an example, a material of the at least one material that has a k-edge absorption energy that is lower than the k-edge absorption energy of Gold is Iron.

According to an example, a material of the at least one material that has a k-edge absorption energy that is lower than the k-edge absorption energy of Gold is a Tungsten-Iron alloy.

In an example, each material layer comprises a Gold layer constituting approximately 8% of the total thickness, a Lead (or Bismuth layer) constituting approximately 72% of the total thickness, and a Tungsten-Iron allow layer constituting approximately 20% of the total thickness. In an example, the total thickness if of the order 250 microns in thickness.

According to an example, the plurality of material layers are laterally spaced from one another by a plurality of resist layers.

According to an example, a thickness of Gold in the material layer of the plurality of material layers is less than 10% of a total thickness of the material layer.

The manufacturing process shown in FIG. 1 uses the LIGA process. Since the main requirement for electroplating is the presence of a conducting surface for starting the process, it is possible to build the gratings using different material and alloys, even if they cannot be deposited by a single electroplating step. Thus a material other than Gold, with a k-edge absorption edge at a higher energy than Gold is filled into trenches using electroplating, providing for cost savings. However, to further improve the grating a relatively small amount of Gold is used to improve the lower energy low transmission. The use of different materials gives to possibility to leverage the presence of k-edges in the different materials. The specific deposition technique discussed uses the LIGA process, but other deposition techniques such as chemical vapour deposition (CVD) or thermal evaporation can be used.

Figure 2:
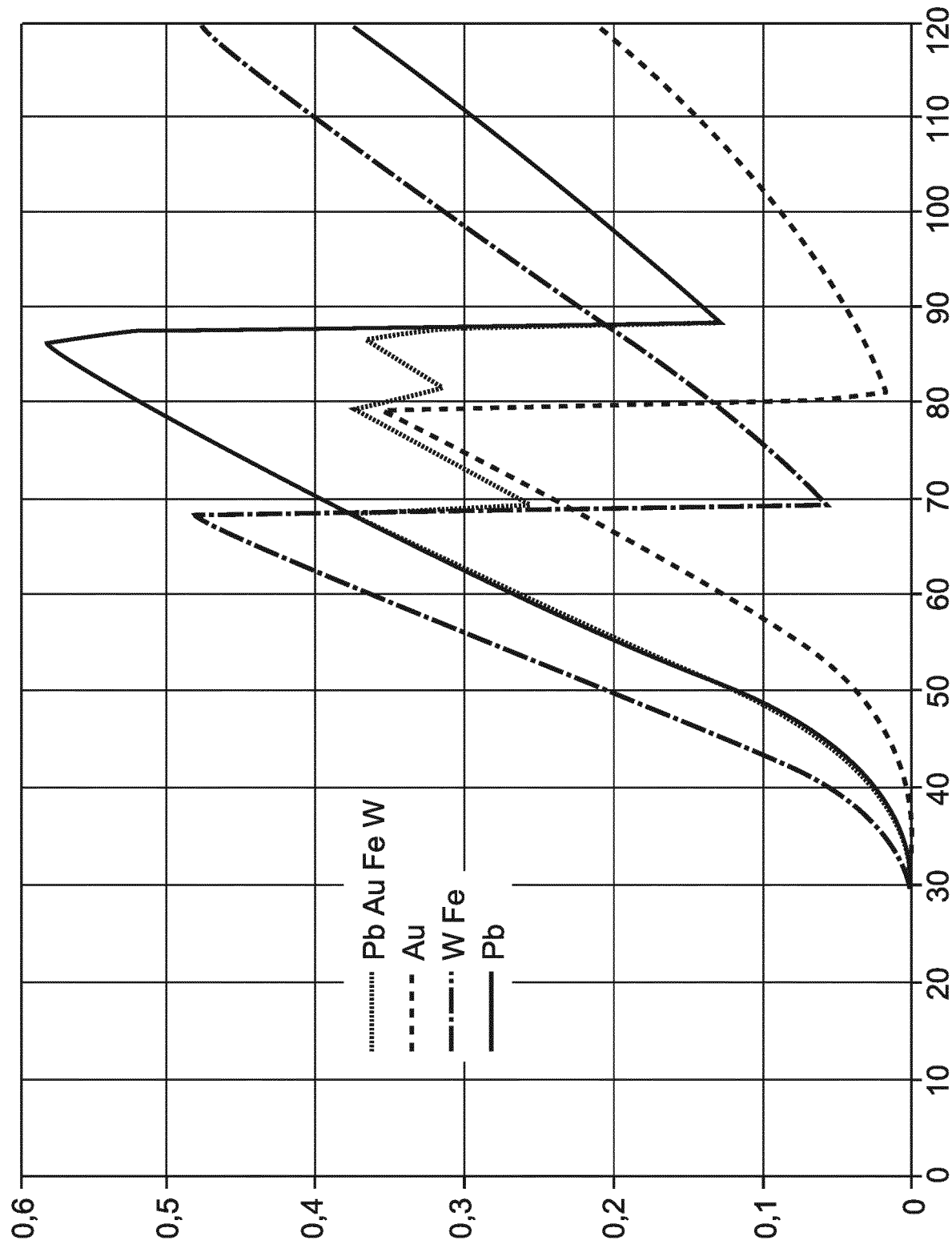
FIG. 2 shows the transmission of different layers each of 250 μum thickness.

FIG. 2 shows example transmission spectra of four grating structures, each with layers 250 μm thick. One grating has layers made from Gold, one with layers made from Lead, and one with layers made from a Tungsten-Iron alloy. A final grating structure has layers made from 180 μm Pb, 50 μm W—Fe and 20 μm Au. Thus a wide band low transmission over the important range of 70 to 89 keV is provided, at reduced cost, with the final grating having an improved a low transmission profile that is better than that for Gold alone and better than that for Lead alone.

Figure 3:
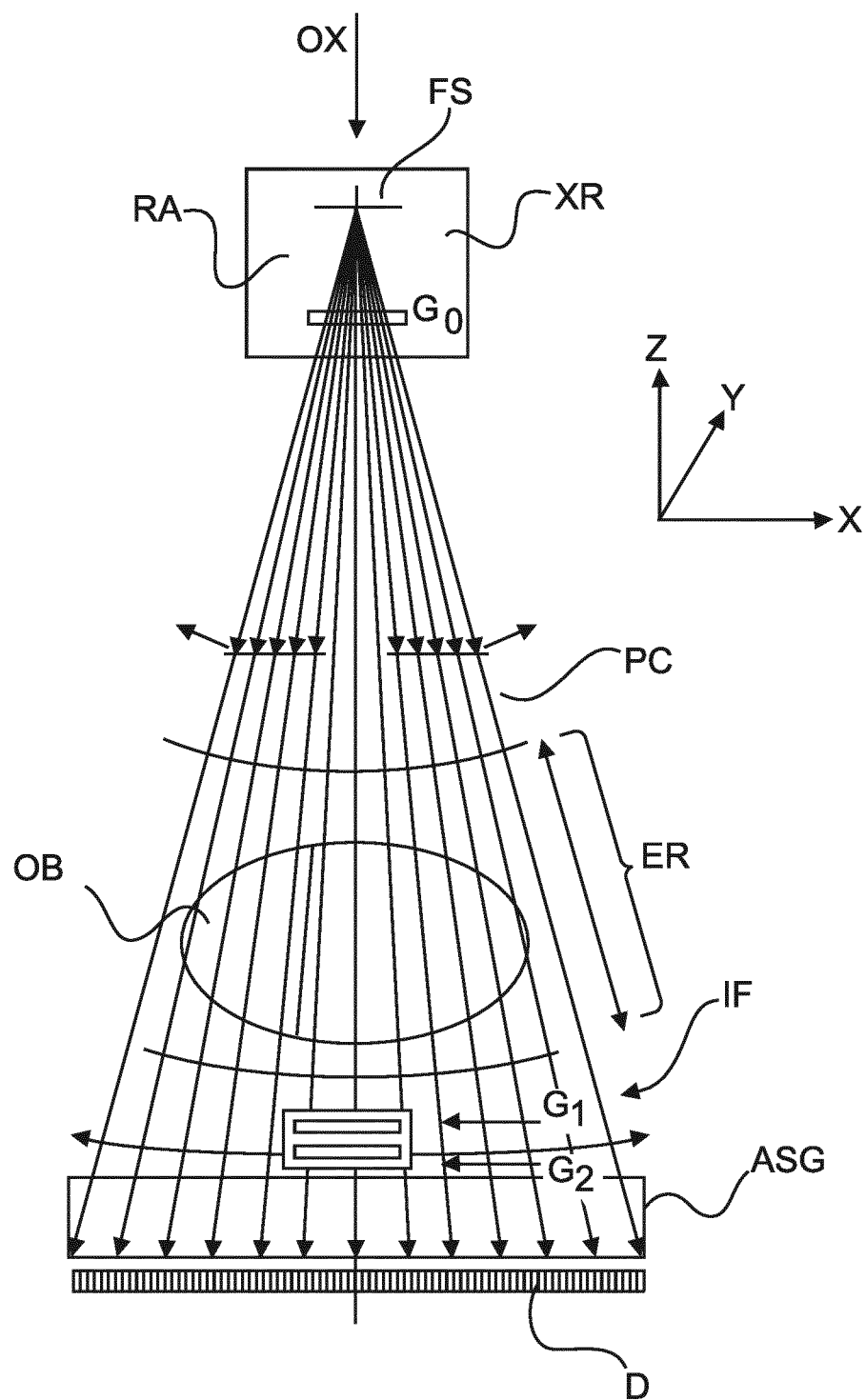
FIG. 3 shows a schematic set up of an example of a phase contrast and/or dark-field imaging system.

To place the grating for X-ray phase contrast and/or dark-field imaging in context, FIG. 3 show an examples of an X-ray phase contrast system that can also acquire dark-field images. The system can also acquire X-ray attenuation images. The system is capable of imaging for the spatial distribution of absorption of, or in, an object OB and also capable of imaging for the spatial distribution of refraction (phase contrast imaging) and also capable of imaging for the spatial distribution of small angle scattering (dark field imaging). The apparatus has a grating based interferometer IF that can be scanned across a stationary X-ray detector D. In this example, the interferometer IF comprises three grating structures G0, G1 and G2, although in other examples a two grating interferometer (having only a gratings G0 and G1 or G1 and G2) is used.

In FIG. 3, the grating G1 is an absorption grating (but also can be a phase shift grating) whereas G2 is an absorption gating. Both gratings have been manufactured as described above with reference to FIG. 1. The system further comprises an X-ray source XR and the X-ray detector D. The X-ray detector D can be a 2D full view X-ray detector, which is either planar or curved. A plurality of detector pixels are arranged in rows and columns as an array to form a 2D X-ray radiation sensitive surface capable of registering X-ray radiation emitted by the X-ray source.

The X-ray detector D and the X-ray source are spaced apart to form an examination region ER. The examination region is suitably spaced to receive the object OB to be imaged. The object may be inanimate or animate. For instance the object may be a piece of luggage or other sample to be imaged, or in a medical context the object may be a human or animal patient or at least an anatomic part of a human or animal.

The interferometric grating structures G1 and G2 are arranged in the examination region ER between the X-ray source XR and X-ray detector D. The X-ray source XR has a focal spot FS from which the X-ray radiation beam emerges. It is the space between the focal spot FS and the X-ray detector's radiation sensitive surface where the two or three grating structures are arranged. The grating G1 is a phase grating and the grating G2 is an analyzer grating. In the example shown, there is in addition to the interferometric gratings G1, G2 of the interferometer IF, a further grating G0 which is the source grating. The source grating G0 has also been manufactured as discussed above with respect to FIG. 1.

The source grating G0 is arranged in proximity of the X-ray source XR, for example at the exit window of a housing of the X-ray tube. The function of the source grating G0 is to make the emitted radiation at least partly coherent. In other words, the source grating G0 can be dispensed with if an X-ray source is used which is capable of producing coherent radiation.

In operation the at least partly coherent radiation passes through the examination region ER and interacts with the object OB. The object then modulates attenuation, refraction, and small angle scattering information onto the radiation which can then be extracted by operation of the grating tandem G1 and G2. The gratings G1, G2 induce an interference pattern which can be detected at the X-ray detector D as fringes of a Moiré pattern. If there was no object in the examination region, there would still be an interference patter observable at the X-ray detector D, called the reference pattern which is normally captured during a calibration procedure. This comes about by especially adjusting or "de-tuning" the mutual spatial relationship between the two gratings G1 and G2 by inducing a slight flexure for instance so that the two gratings are not perfectly parallel. Now, if the object is positioned in the examination region and interacts with the radiation as mentioned, the Moiré pattern, which is now more appropriately called the object pattern, can be understood as a disturbed version of the reference pattern. This difference from the reference pattern can then be used to compute one or all of the phase contrast, dark field images.

Continuing with FIG. 3, to be able to acquire suitable signals from which the images can be computed, a scanning motion is performed by the grating tandem G1-G2. As a result of this motion, at each pixel of the X-ray detector D a series of intensity values are detected. For good results, the detuning of the gratings G1, G2 is such that a period of the Moiré pattern should extend for a few of its cycles (two or three) in the direction of the scan motion. For each X-ray detector pixel, the series of intensity values can then be fitted to a (sinusoidal) signal forward model, for example, in order to derive the respective contributions of refraction, absorption, and small angle scatter. This type of signal processing is done in a signal processing unit not shown in FIG. 3, but which is known to the skilled person. The X-ray detector D remains stationary for any given orientation of the optical axis OX which is shown in FIG. 3 to extend along the Z axis. In other words, the X-ray detector D is kept stationary (at least during an image acquisition operation) with respect to an arbitrary reference point in the examination region. The interferometric setup as described above is what is commonly referred to as a Talbot-Lau interferometer. The distances between G0 and G1 and between G1 and G2 must be finely tuned to fit the requirements of Talbot distance which in turn is a function of the "pitch" (that is, the spatial period of the grating rulings) of the respective grating. Moving the interferometer IF relative to the X-ray detector D may cause a slight change in fringe distribution due to fringe drift. However, the fringe drift can be compensated by relating such drift to the fringe drift as obtained with a reference scan. Such reference scan may be a blank scan performed at the installation of the X-ray imaging apparatus.

The alignment of the gratings as described above is very difficult, and becomes more difficult as the layer height of the gratings increases. The gratings made by the present manufacturing method can have a reduced height, leading to a relaxation of the alignment process and enabling for easier system configuration.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A diffraction grating for X-ray phase contrast and/or dark-field imaging, the grating comprising:
   a substrate; and
   a plurality of material layers formed on a surface of the substrate and laterally spaced from each other across the surface of the substrate;
   wherein a material layer of the plurality of material layers comprises a plurality of materials formed one on top of another in a direction perpendicular to the surface of the substrate;
   wherein the plurality of materials comprises at least one material that has a k-edge absorption energy that is higher than the k-edge absorption energy of Gold and comprises Gold; and
   wherein a thickness of Gold in the material layer of the plurality of material layers is less than approximately 30% of a total thickness of the material layer.

2. The grating according to claim 1, wherein a material of the at least one material that has a k-edge absorption energy that is higher than the k-edge absorption energy of Gold is Lead.

3. The grating according to claim 1, wherein a material of the at least one material that has a k-edge absorption energy that is higher than the k-edge absorption energy of Gold is Bismuth.

4. The grating according to claim 1, wherein the plurality of materials comprises at least one material that has a k-edge absorption energy that is lower than the k-edge absorption energy of Gold.

5. The grating according to claim 4, wherein a material of the at least one material that has a k-edge absorption energy that is lower than the k-edge absorption energy of Gold is Tungsten.

6. The grating according to claim 4, wherein a material of the at least one material that has a k-edge absorption energy that is lower than the k-edge absorption energy of Gold is Iron.

7. The grating according to claim 4, wherein a material of the at least one material that has a k-edge absorption energy that is lower than the k-edge absorption energy of Gold is a Tungsten-Iron alloy.

8. The grating according to claim 1, wherein the plurality of material layers are laterally spaced from one another by a plurality of resist layers.

9. The grating according to claim 1, wherein a thickness of Gold in the material layer of the plurality of material layers is less than approximately 10% of a total thickness of the material layer.

10. An X-ray phase contrast and/or dark-field imaging system, comprising:
    an X-ray source;
    an X-ray detector; and
    a diffraction grating comprising:
        a substrate; and
        a plurality of material layers formed on a surface of the substrate and laterally spaced from each other across the surface of the substrate, wherein a material layer of the plurality of material layers comprises a plurality of materials formed one on top of another in a direction perpendicular to the surface of the substrate, wherein the plurality of materials comprises at least one material that has a k-edge absorption energy that is higher than the k-edge absorption energy of Gold and comprises Gold, and wherein a thickness of Gold in the material layer of the plurality of material layers is less than approximately 30% of a total thickness of the material layer.

11. A method of manufacturing a grating for X-ray phase contrast and/or dark-field imaging, the method comprising:
    forming a photo-resist layer on a surface of a substrate;
    illuminating the photo-resist layer with radiation using a mask representing a desired grating structure;
    etching the photo-resist layer to remove parts of the photo-resist layer to leave a plurality of trenches that are laterally spaced from each other across the surface of the substrate;
    forming a plurality of material layers on the surface of the substrate, wherein each layer is formed in a trench, wherein a material layer comprises a plurality of materials, wherein the plurality of materials are formed one on top of another in a direction perpendicular to the surface of the substrate, and wherein the plurality of materials comprises at least one material that has a k-edge absorption energy that is higher than the k-edge absorption energy of Gold and comprises Gold; and
    wherein a thickness of Gold in the material layer of the plurality of material layers is less than approximately 30% of a total thickness of the material layer.

12. The method according to claim 11, wherein at least one material that has a k-edge absorption energy that is higher than the k-edge absorption energy of Gold is at least one of Lead and Bismuth.

13. The method according to claim 11, wherein the plurality of materials comprises at least one material that has a k-edge absorption energy that is lower than the k-edge absorption energy of Gold.

14. The method according to claim 13, wherein the at least one material that has a k-edge absorption energy that is lower than the k-edge absorption energy of Gold is at least one of Tungsten, Iron, and a Tungsten-Iron alloy.

15. The method according to claim 11, further comprising removing a plurality of resist layers that are between the plurality of material layers.

* * * * *